(12) United States Patent
Iyobe et al.

(10) Patent No.: US 7,371,730 B2
(45) Date of Patent: May 13, 2008

(54) CRYSTALS OF GLUCOPYRANOSYLOXYBENZYL BENZENE DERIVATIVE

(75) Inventors: Akira Iyobe, Nagano (JP); Hirotaka Teranishi, Nagano (JP); Kazuya Tatani, Nagano (JP); Shigeru Yonekubo, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 537 days.

(21) Appl. No.: 10/507,611

(22) PCT Filed: Mar. 4, 2003

(86) PCT No.: PCT/JP03/02466

§ 371 (c)(1),
(2), (4) Date: Sep. 14, 2004

(87) PCT Pub. No.: WO03/080635

PCT Pub. Date: Oct. 2, 2003

(65) Prior Publication Data

US 2005/0119192 A1    Jun. 2, 2005

(30) Foreign Application Priority Data

Mar. 22, 2002  (JP) ............................. 2002-081038

(51) Int. Cl.
*A01N 43/04* (2006.01)
*A61K 31/70* (2006.01)
*C07H 15/00* (2006.01)
*C07H 15/24* (2006.01)

(52) U.S. Cl. ........................... 514/25; 514/27; 536/4.1; 536/18.1

(58) Field of Classification Search ..................... None
See application file for complete search history.

(56) References Cited

U.S. PATENT DOCUMENTS 6,683,056 B2 * 1/2004 Washburn et al. ............ 514/25

FOREIGN PATENT DOCUMENTS

| WO | WO 01/68660 A1 | 9/2001 |
| WO | WO 01/74834 A1 | 10/2001 |
| WO | WO 02/28872 A1 | 4/2002 |
| WO | WO 03/080635 A1 | 10/2003 |

* cited by examiner

*Primary Examiner*—Shaojia Anna Jiang
*Assistant Examiner*—Traviss C. McIntosh, III
(74) *Attorney, Agent, or Firm*—Sughrue Mion, PLLC

(57) ABSTRACT

The present invention provides crystals of 2-(4-methoxybenzyl)phenyl 6-O-ethoxycarbonyl-β-D-glucopyranoside, pharmaceutical compositions containing the same and their uses, which exhibit excellent SGLT2 inhibitory activities, and are useful for treating or preventing diseases associated with hyperglycemia.

6 Claims, 2 Drawing Sheets

CRYSTALS OF GLUCOPYRANOSYLOXYBENZYL BENZENE DERIVATIVE

TECHNICAL FIELD

The present invention relates to crystals of 2-(4-methoxybenzyl)phenyl 6-O-ethoxycarbonyl-β-D-glucopyranoside and their uses.

BACKGROUND ART 2-(4-Methoxybenzyl)phenyl 6-O-ethoxycarbonyl-β-D-glucopyranoside represented by formula (I):

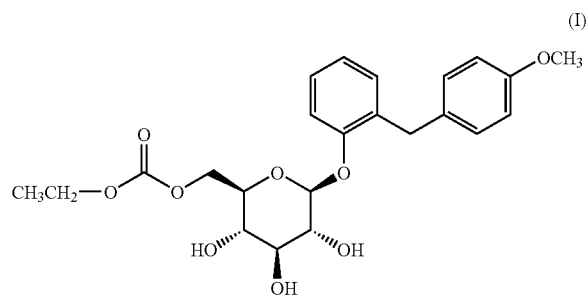

is a novel compound not known in literatures, which has been found by the present applicant. This compound is converted to an active form of 2-(4-methoxybenzyl)phenyl β-D-gluco-pyranoside in vivo, which exhibits excellent inhibitory activities against SGLT2 and is useful for the treatment or prevention of diseases associated with hyperglycemia such as diabetes mellitus, diabetic complication, obesity and the like. None of crystalline form of this compound has been known so far.

DISCLOSURE OF THE INVENTION 2-(4-Methoxybenzyl)phenyl 6-O-ethoxycarbonyl-β-D-glucopyranoside could have been prepared only in an amorphous form up to now. For preparing the amorphous form of said compound in high purity, troublesome purification steps havebeen required. Moreover, the amorphous form of said compound has unsatisfactory stabilities, and is difficult to prepare formulations due to its viscous property.

The present inventors intensively investigated for crystalline forms of 2-(4-methoxybenzyl)phenyl 6-O-epoxycarbonyl-β-D-glucopyranoside which have good storage stability and are suitable for formulating, and had found that 2-(4-methoxybenzyl)phenyl 6-O-ethoxycarbonyl-β-D-glucopyranoside had two crystalline forms, "crystalline form α" and "crystalline form β". Moreover, the present inventors had found unexpectedly that these crystalline forms could be prepared in high purities by a convenient purification procedure, and had good storage stabilities and flowabilities, and accordingly are suitable for formulating. Based on these findings, the present invention has been accomplished.

The present invention therefore provides:
(1) a crystal of 2-(4-methoxybenzyl)phenyl 6-O-ethoxycarbonyl-β-D-glucopyranoside;
(2) a crystal of 2-(4-methoxybenzyl)phenyl 6-O-ethoxycarbonyl-β-D-glucopyranoside, which shows an X-ray powder diffraction pattern having characteristic peaks at a diffraction angle (2θ±0.1) of 5.6, 13.8, 14.6, 16.8, 17.7 and 20.8 degrees (hereinafter, referred to as "crystalline form α");
(3) a crystal of 2-(4-methoxybenzyl)phenyl 6-O-ethoxycarbonyl-β-D-glucopyranoside, which shows an X-ray powder diffraction pattern having characteristic peaks at a diffraction angle (2θ±0.1) of 4.7, 5.5, 7.3, 8.6, 14.5 and 16.7 degrees (hereinafter, referred to as "crystalline form β");
(4) a pharmaceutical composition which comprises, as an active ingredient, a crystal according to any one of the above (1) to (3);
(5) the pharmaceutical composition according to the above (4), for the prevention or treatment of a disease associated with hyperglycemia;
(6) a use of a crystal according to any one of the above (1) to (3), for the manufacture of a medicament for preventing or treating a disease associated with hyperglycemia;
(7) a method for preventing or treating a disease associated with hyperglycemia, which comprises administering a therapeutically effective amount of a crystal according to any one of the above (1) to (3).

BEST MODE FOR CARRYING OUT THE INVENTION

Figure 1:
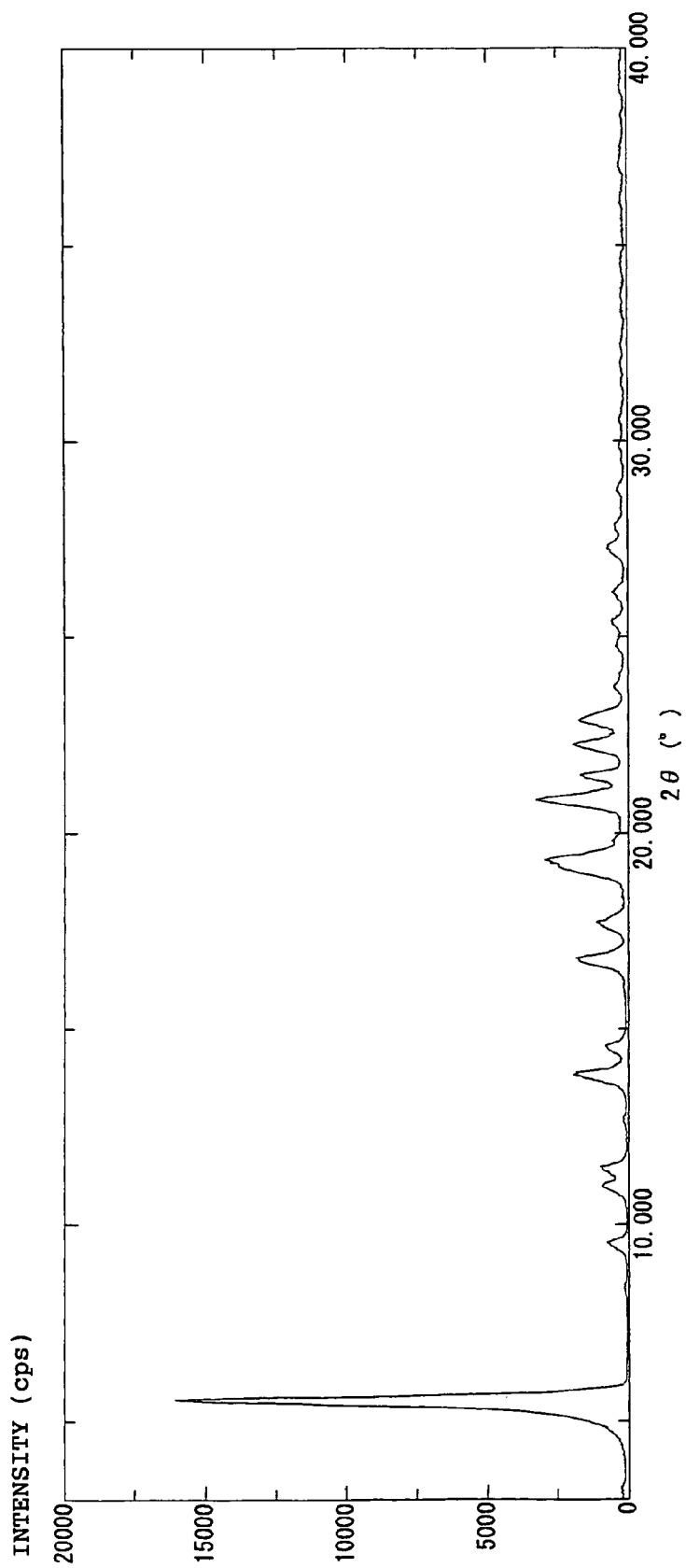
FIG. 1 is an X-ray powder diffraction pattern of crystalline form α of 2-(4-methoxybenzyl)phenyl 6-O-ethoxycarbonyl-β-D-glucopyranoside prepared in Example 1, where the ordinate shows the X-ray intensity in cps and the abscissa shows the diffraction angle in 2θ.

Crystalline forms α and β of the present invention can be prepared as follows.

Crystals of 2-(4-methoxybenzyl)phenyl 6-O-ethoxycarbonyl-β-D-glucopyranoside were firstly obtained by dissolving an amorphous form of said compound in ethanol under heating, and then scratching a wall of a vessel for crystallization under ice-cooling. The crystals were obtained in a mixture of crystalline forms α and β. The present inventors had eagerly studied for crystallizing conditions and found that crystalline forms α and β of the present invention could be prepared in a pure crystalline form by crystallizing from a particular solvent as described below.

Crystalline form α of the present invention can be prepared as follows. An arbitrary form of 2-(4-methoxybenzyl)phenyl 6-O-ethoxycarbonyl-β-D-glucopyranoside is dissolved in a suitable first solvent (also referred to as "good solvent") under heating. Thereafter, to the solution is added, if required, a second solvent (also referred to as "poor solvent"), and the resulting mixture is stirred or stood for crystallization. The precipitated crystals are collected and dried to afford crystalline form α. Examples of first solvents include ethanol, isopropanol, ethyl acetate, acetone or methyl ethyl ketone, which can be used singly or as a mixture of one or more solvents. The amount of first solvents is varied depending on the type of the solvent, and is ordinarily in the range of about 2 to about 20 parts by weight on the basis of a part by weight of 2-(4-methoxybenzyl)phenyl 6-O-ethoxycarbonyl-β-D-glucopyranoside.

Examples of second solvents, which can be miscible with a solution of said compound in a first solvent, include hexane, heptane or water. The amount of second solvents is varied depending on the type of the solvent, and is ordinarily in the range of about 0.1 to about 5 parts by weight on the basis of apart by weight of a first solvent. The crystallizing temperature for crystalline form α is ordinarily below about 50° C., preferably in the range of about 20 to about 50° C. The crystallizing time is varied depending on the crystallizing temperature, and is ordinarily in the range of about 1 to about 24 hours.

Crystalline form β of the present invention can be prepared as follows. An arbitrary form of 2-(4-methoxybenzyl) phenyl 6-O-ethoxycarbonyl-β-D-glucopyranoside is dissolved in methanol, the amount of which is ordinarily in the range of about 3 to about 10 parts by weight, preferably about 4 to about 6 parts by weight on the basis of a part by weight of 2-(4-methoxybenzyl)phenyl 6-O-ethoxycarbonyl-β-D-glucopyranoside. Thereafter, the solution is concentrated under reduced pressure at a temperature of about 30 to about 40° C. for crystallization, and the precipitated crystals are collected and dried to afford crystalline form β. Alternatively, crystalline form β can be prepared by heating an amorphous form of 2-(4-methoxybenzyl) phenyl 6-O-ethoxycarbonyl-β-D-glucopyranoside at a temperature of about 120 to about 140° C. for about 1 to about 4 hours.

Figure 2:
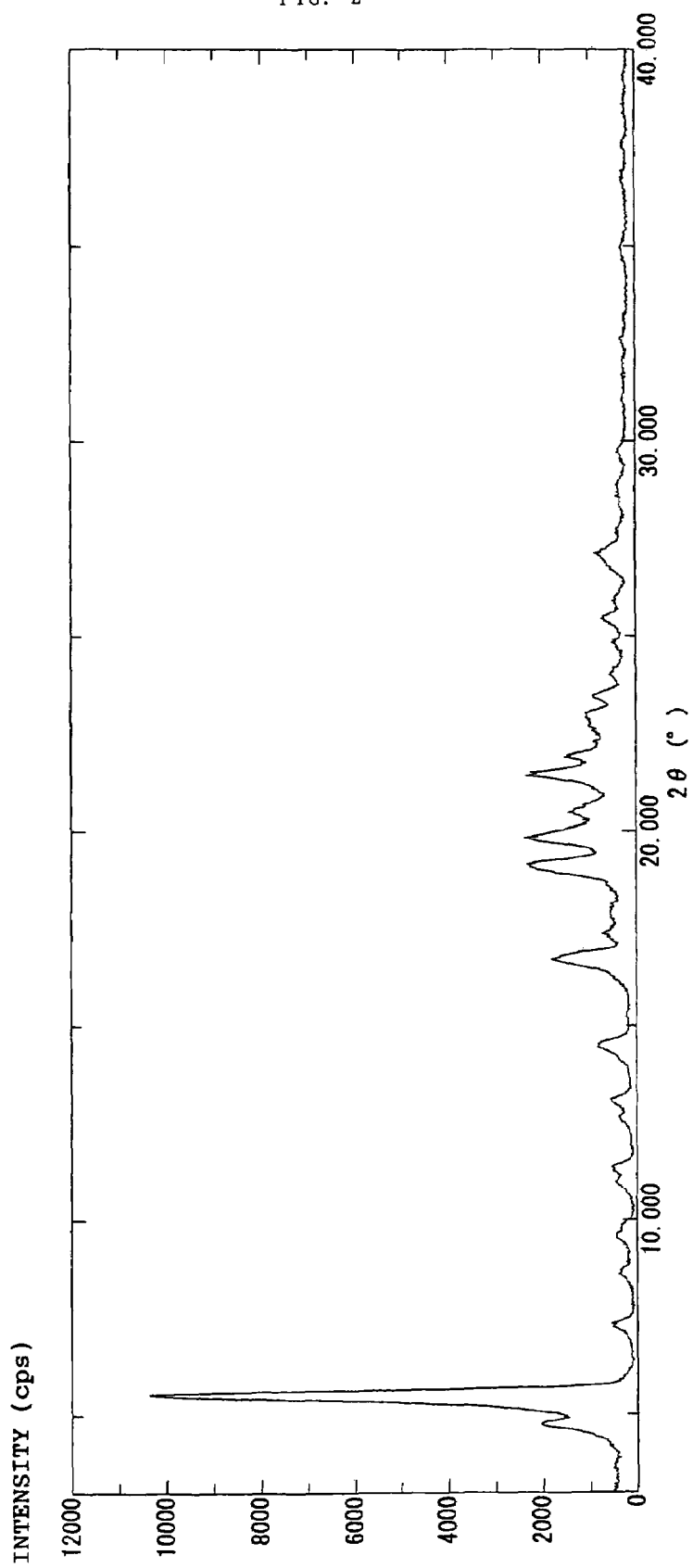
FIG. 2 is an X-ray powder diffraction pattern of crystalline form β of 2-(4-methoxybenzyl)phenyl 6-O-ethoxycarbonyl-β-D-glucopyranoside prepared in Example 4, where the ordinate shows the X-ray intensity in cps and the abscissa shows the diffraction angle in 2θ.

Crystalline forms α and β thus obtained can be identified by their characteristic diffraction peaks as shown in the X-ray powder diffraction charts of FIG. 1 or 2;
(1) crystalline form α has characteristic peaks at a diffraction angle (2θ±0.1) of 5.6, 13.8, 14.6, 16.8, 17.7 and 20.8 degrees as illustrated in FIG. 1;
(2) crystalline form β has characteristic peaks at a diffraction angle (2θ±0.1) of 4.7, 5.5, 7.3, 8.6, 14.5 and 16.7 degrees as illustrated in FIG. 2.

Crystalline forms α and β of the present invention can be stored under ordinarily storage conditions such as 25° C./60% relative humidity and the like for a long period without changing their crystalline forms, and are also chemically stable. Crystalline forms α and β of the present invention have excellent flow abilities and good handling properties, and can be formulated into powders, fine granules, granules, tablets, capsules or the like according to conventional methods.

In the case of using a pharmaceutical composition comprising a crystal of the present invention as an active ingredient, various dosage forms can be administered depending upon their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to conventional formulation procedures depending upon their dosage forms.

In the case of using a pharmaceutical composition for a medical treatment, the dosage of a crystal of the present invention as an active ingredient is appropriately determined depending on the age, sex or body weight of the individual patient, the severity of the disease, the condition to be treated and the like. A typical dosage for oral administration is in the range of from about 0.1 mg to about 1000 mg per day per adult human. A typical dosage for parenteral administration is in the range of from about 0.01 mg to about 300 mg per day per adult human. The dosages may be administered in single or divided doses, for example one to several times daily.

EXAMPLE

The following examples, reference examples and test examples illustrate the invention in further detail. It is to be understood, however, that they are not to be construed as limiting the scope of the invention in any way.

X-ray powder diffraction patterns of each crystalline form were obtained using an X-ray diffraction analyzer, RINT2100 (Rigaku) which was operated at a tube voltage of 40 kV and a tube electric current of 40 mA, and using Cu beam.

Reference Example 1

2-(4-Methoxybenzyl)phenyl 2,3,4,6-tetra-O-acetyl-β-D-glucopyranoside

To a solution of 2-(4-methoxybenzyl)phenol (46 mg) and 2,3,4,6-tetra-O-acetyl-1-O-trichloroacetoimdoyl-α-D-glucopyranose (0.13 g) in dichloromethane (2 mL) was added boron trifluoride diethyl ether complex (0.033 mL), and the mixture was stirred at room temperature for 1 hour. The reaction mixture was purified by column chromatography on aminopropyl silica gel (eluent:dichloromethane) to give 2-(4-methoxybenzyl)phenyl 2,3,4,6-terta-O-acetyl-β-D-glucopyranoside (0.11 g). $^1$H-NMR (CDCl$_3$) δ ppm: 1.91 (3H, s), 2.03 (3H, s), 2.05 (3H, s), 2.08 (3H, s), 3.77 (3H, s), 3.80-3.95 (3H, m), 4.17 (1H, dd, J=2.5, 12.2 Hz), 4.29 (1H, dd, J=5.5, 12.2 Hz), 5.11 (1H, d, J=7.5 Hz), 5.10-5.25 (1H, m), 5.25-5.40 (2H, m), 6.75-6.85 (2H, m), 6.95-7.10 (5H, m), 7.10-7.25 (1H, m)

Reference Example 2

2-(4-Methoxybenzyl)phenyl β-D-glucopyranoside

Sodiummethoxide (28% methanol solution; 0. 12 mL) was added to a solution of 2-(4-methoxybenzyl)phenyl 2,3,4,6-tetra-O-acetyl-β-D-glucopyranoside (0.11 g) in methanol (4 mL), and the mixture was stirred at room temperature for 30 minutes. The solvent was removed under reduced pressure. The residue was purified by column chromatography on silica gel (eluent:dichloromethane/methanol=10/1) to give 2-(4-methoxy-benzyl)phenyl β-D-glucopyranoside (65 mg). $^1$H-NMR (CD$_3$OD) δ ppm: 3.35-3.55 (4H, m), 3.69 (1H, dd, J=5.1, 12.1 Hz), 3.73 (3H, s), 3.80-4.00 (2H, m), 4.03 (1H, d, J=15.1 Hz), 4.91 (1H, d, J=7.4 Hz), 6.75-6.85 (2H, m), 6.85-6.95 (1H, m), 6.95-7.10 (1H, m), 7.10-7.20 (4H, m)

Reference Example 3

2-(4-Methoxybenzyl)phenyl 6-O-ethoxycarbonyl-β-D-glucopyranoside

To a solution of 2-(4-methoxybenzyl)phenyl β-D-glucopyranoside (0.075 g) in 2,4,6-trimethylpyridine (2 mL) was added ethyl chloroformate (0.04 mL) at room temperature. After the mixture was stirred at room temperature for 16 hours, a saturated aqueous solution of citric acid was added to the reaction mixture, and the mixture was extracted with ethyl acetate. The extract was washed with water and dried over anhydrous magnesium sulfate, and the solvent was removed under reduced pressure. The residue was purified by preparative thin layer chromatography on silica gel (eluent:dichloromethane/methanol=10/1) to give an amorphous form of 2-(4-methoxybenzyl)phenyl 6-O-ethoxycarbonyl-β-D-glucopyranoside (0.032 g). As a result of X-ray powder diffraction analysis, the amorphous substance shows no distinct peak. $^1$H-NMR (CD$_3$OD) δ ppm: 1.23 (3H, t, J=7.1 Hz), 3.30-3.65 (4H, m), 3.74 (3H, s), 3.93 (1H, d, J=15.1 Hz), 4.02 (1H, d, J=15.1 Hz), 4.05-4.20 (2H, m), 4.29 (1H, dd, J=6.4,11.7 Hz), 4.45 (1H, dd, J=2.2, 11.7 Hz), 4.89 (1H, d, J=7.4 Hz), 6.75-6.85(2H, m), 6.85-7.05 (2H, m), 7.05-7.2 (4H, m)

Example 1

Crystalline form α of 2-(4-methoxybenzyl)phenyl 6-O-ethoxycarbonyl-β-D-glucopyranoside To a stirred solution of 2-(4-methoxybenzyl)phenyl β-D-glucopyranoside (220 g) and 2,6-lutidine (136 mL) in acetone (834 mL) was added ethyl chloroformate (84 mL) at about 5 to about 10° C. Thereafter the mixture was stirred at about 10 to about 20° C. for 4 hours. To the reaction mixture were added water and ethyl acetate, and the organic layer was separated. The organic layer was washed successively with a 10% aqueous solution of citric acid, brine, a 10% aqueous solution of sodium bicarbonate and brine, and dried over anhydrous sodium sulfate. The desiccant was removed by filtration, and the solvent of the filtrate was removed under reduced pressure. The residue (326 g) was dissolved in ethanol (1039 mL) under heating, and the resulting solution was treated with activated charcoal (11 g). After the mixture was stirred for 5 minutes, insoluble materials were filtered through celite. To the filtrate was added n-hexane (2046 mL) at about 30 to about 40° C. over about 45 minutes, and the resulting mixture was allowed to stand at room temperature for 17 hours. Thereafter, the mixture was stirred under ice-cooling for 2 hours, and the precipitated crystals were collected by filtration to afford crude crystals of 2-(4-methoxybenzyl)phenyl 6-O-ethoxycarbonyl-β-D-glucopyranoside (202 g).

The same procedure as described above using another 2-(4-methoxybenzyl)phenyl β-D-glucopyranoside (220 g) and 2,6-lutidine (136 mL) gave crude crystals of 2-(4-methoxybenzyl)phenyl 6-O-ethoxycarbonyl-β-D-glucopyranoside (200 g). The crude crystals were combined, and a 300 g portion of the crude crystals, isopropanol (4260 mL) and methyl ethyl ketone (225 mL) were heated with stirring until it appeared to be a clear solution. The solution was treated with activated charcoal (15 g), and the mixture was stirred for 15 minutes and filtered. To the filtrate were seeded crystals of crystalline form α at about 50° C., and the mixture was cooled to about 35° C. during 1 hour with stirring. Thereafter, the mixture was allowed to stand overnight, and then was stirred under ice-cooling for 2 hours. The precipitated crystals were collected by filtration, washed with cold isopropanol, and dried at about 60° C. for 12 hours under reduced pressure to afford 240 g of crystals.

As a result of X-ray powder diffraction analysis, the crystals were identified as crystalline form α. An X-ray powder diffraction pattern of the crystals was shown in FIG. 1.

Example 2

Crystalline form α of 2-(4-methoxybenzyl)phenyl 6-O-ethoxycarbonyl-β-D-glucopyranoside A mixture of 2-(4-methoxybenzyl)phenyl 6-O-ethoxycarbonyl-β-D-glucopyranoside (5.0 g) and ethanol (30 mL) was heated at 60 to 65° C. with stirring until it appeared to be a clear solution. The solution was allowed to cool to 40 to 45° C., and stirred at the same temperature for 1 hour and at 20 to 30° C. for another 1 hour. The precipitated crystals were collected by filtration, and dried at about 70° C. for 4 hours under reduced pressure to afford 3.33 g of crystals.

As a result of X-ray powder diffraction analysis, the crystals were identified as crystalline form α.

Example 3

Crystalline form α of 2-(4-methoxybenzyl)phenyl 6-O-ethoxycarbonyl-β-D-glucopyranoside A mixture of 2-(4-methoxybenzyl)phenyl 6-O-ethoxycarbonyl-β-D-glucopyranoside (90.0 g) and acetone (300 mL) was heated at 40 to 45° C. with stirring until it appeared to be a clear solution. The solution was allowed to cool to 35° C., and n-hexane (300 mL) was added thereto at 25 to 35° C. The mixture was stirred at a temperature of 30 to 35° C. for 15 minutes, and another n-hexane (300 mL) was added over 20 minutes. Moreover, n-hexane (300 mL) was added over 5 minutes, and the resulting mixture was stirred at room temperature overnight. The precipitated crystals were collected by filtration, washed with acetone/n-hexane (1:3), and dried at about 70° C. for 5 hours under reduced pressure to afford 81.9 g of crystals.

As a result of X-ray powder diffraction analysis, the crystals were identified as crystalline form α.

Example 4

Crystalline form β of 2-(4-methoxybenzyl)phenyl 6-O-ethoxycarbonyl-β-D-glucopyranoside The amorphous form of 2-(4-methoxybenzyl)phenyl 6-O-ethoxycarbonyl-β-D-glucopyranoside (5.0 g) obtained in Reference Example 3 was placed in an oven, and heated at 125° C. for 3 hours. After allowed to cool to room temperature, 4.9 g of crystals were obtained.

As a result of X-ray powder diffraction analysis, the crystals were identified as crystalline form β. An X-ray powder diffraction pattern of the crystals was shown in FIG. 2.

Example 5

Crystalline form β of 2-(4-methoxybenzyl)phenyl 6-O-ethoxycarbonyl-β-D-glucopyranoside A mixture of 2-(4-methoxybenzyl)phenyl 6-O-ethoxycarbonyl-β-D-glucopyranoside (1.0 g) and methanol (5 mL) was heated with stirring, until it appeared to be a clear solution. The solution was concentrated under reduced pressure to dryness. The precipitated crystals were collected, and dried at about 70° C. for 5 hours under reduced pressure to afford 0.9 g of crystals.

As a result of X-ray powder diffraction analysis, the crystals were identified as crystalline form β.

Test Example 1

Stability Test

Stability tests were carried out under the following conditions for crystalline forms α and β. Residual percentages of test substances were determined by HPLC, and changes in crystalline form were examined by X-ray powder diffraction analysis.

HPLC conditions:
  detection; 225 nm
  column; Inertsil ODS-3
  column temperature; 30° C.
  mobile phase; 0.02 mol/L phosphate buffer (pH 3.0): acetonitrile=58:42→30:70
  flow rate; 1.0 mL/min.

Storage conditions:
  1) 40° C./75% RH, 2 months, stopper tightly
  2) 60° C., 2 months, stopper tightly As a result, crystalline forms α and β of the present invention indicate no change in their crystalline forms and residual percentage, and have excellent storage stabilities.

Test Example 2

Assay for Inhibitory Effect on Human SGLT2 Activity

1) Construction of the plasmid vector expressing human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the Pfu DNA Polymerase (Stratagene)-used PCR reaction, in which the human kidney cDNA library described above was used as the template and the following oligo nucleotides 0702F and 0712R, presented as SEQ ID NO:1 and SEQ ID NO:2 respectively, were used as the primers. The amplified DNA fragment was ligated into pCR-Blunt (Invitrogen), a vector for cloning, according to standard method of the kit. The competent cell, *Escherichia coli* HB101 (Toyobo), was transformed according to usual method and then selection of the transformants was performed on the LB agar medium containing 50 µg/mL of kanamycin. After the plasmid DNA was extracted and purified from the one of the transformants, amplifying of the DNA fragment coding for human SGLT2 was performed by the Pfu DNA Polymerase (Stratagene)-used PCR reaction, in which the following oligo nucleotides 0714F and 0715R, presented as SEQ ID NO:3 and SEQ ID NO:4 respectively, were used as the primers. The amplified DNA fragment was digested with restriction enzymes, Xho I and Hind III, and then purified with Wizard Purification System (Promega). This purified DNA fragment was inserted at the corresponding multi-cloning sites of pcDNA3.1 (-) Myc/His-B (Invitrogen), a vector for expressing of fusion protein. The competent cell, *Escherichia coli* HB101(Toyobo), was transformed according to usual method and then selection of the transformant was performed on the LB agar medium containing 100 µg/mL of ampicillin. After the plasmid DNA was extracted and purified from this transformant, the base sequence of the DNA fragment inserted at the multi-cloning sites of pcDNA3.1 (-) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459-465 (1992)). Sequentially, a clone in which valine is substituted for the isoleucine-433 was obtained. This plasmid vector expressing human SGLT2 in which the peptide presented as SEQ ID NO:5 is fused to the carboxyl terminal alanine residue was designated KL29.

```
SEQ ID NO:1    ATGGAGGAGCACACAGAGGC
SEQ ID NO:2    GGCATAGAAGCCCCAGAGGA
SEQ ID NO:3    AACCTCGAGATGGAGGAGCACACAGAGGC
SEQ ID NO:4    AACAAGCTTGGCATAGAAGCCCCAGAGGA
SEQ ID NO:5    KLGPEQKLISEEDLNSAVDHHHHHH
```

2) Preparation of the cells expressing transiently human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 µF, $2\times10^6$ cells of COS-7 cell and 20 µg of KL29 in 500 µL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 µL of this cell suspension was added. After overnight culture at 37° C. under 5% $CO_2$, 125 µL of DMEM medium which is containing 10% of fetal bovine serum (Sanko Jyunyaku), 100 units/mL sodium penicillin G (Gibco-BRL: LIFE TECHNOLOGIES), 100 µg/mL streptomycin sulfate (Gibco-BRL: LIFE TECHNOLOGIES) was added to each well. After a culture until the following day, these cells were used for the measurement of the inhibitory activity against the uptake of methyl-α-D-glucopyranoside.

3) Measurement of the inhibitory activity against the uptake of methyl-α-D-glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), each diluent was used as test sample for measurement of the inhibitory activity. After removal of the medium of the COS-7 cells. expressing transiently human SGLT2, to each well 200 µL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added, and the cells were incubated at 37° C. for 10 minutes. After the pretreatment buffer was removed, 200 µL of the same buffer was added again, and the cells were incubated at 37° C. for 10 minutes. The buffer for measurement was prepared by adding of 7 µL of methyl-α-D-(U-14C) glucopyranoside (Amersham Pharmacia Biotech) to 525 µL of the prepared test sample. For the control, the buffer for measurement without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 µL of the buffer for measurement was added to each well, the cells were incubated at 37° C. for 2 hours. After the buffer for measurement was removed, 200 μL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris (hydroxymethyl)aminomethane) was added to each well and immediately removed. After two additional washing, the cells were solubilized by addition of 75 μL of 0.2 N sodium hydroxide to each well. After the cell lysates were transferred to the PicoPlate (Packard) and 150 μL of MicroScint-40 (Packard) was added to each well, the radioactivity was measured with microplate scintillation counter TopCount (Packard). The difference in uptake was obtained as 100% value by subtracting the radioactivity in the basal uptake from that in control and then the concentrations at which 50% of uptake was inhibited ($IC_{50}$ Value) were calculated from the concentration-inhibition curve by least square method. The result is shown in the following Table 1.

TABLE 1

| Test compound | $IC_{50}$ value (nM) |
|---|---|
| Reference Example 2 | 350 |

INDUSTRIAL APPLICABILITY

Crystalline forms α and β of the present invention can be prepared in high purity by a convenient purification procedure, and are suitable for a commercial production. Crystalline forms α and β of the present invention has good storage stabilities, and are suitable for producing and supplying a constant quality of medicaments. Furthermore, crystalline forms α and β of the present invention has good flow abilities and handling properties, and are suitable for formulation. Therefore, crystalline forms α and β of the present invention are useful as a drug substance.

The invention claimed is:

1. A crystal of 2-(4-methoxybenzyl)phenyl 6-O-ethoxycarbonyl-β-D-glucopyranoside, which shows an X-ray powder diffraction pattern having characteristic peaks at a diffraction angle (2θ±0.1) of 5.6, 13.8, 14.6, 16.8, 17.7 and 20.8 degrees.

2. A crystal of 2-(4-methoxybenzyl)phenyl 6-O-ethoxycarbonyl-β-D-glucopyranoside, which shows an X-ray powder diffraction pattern having characteristic peaks at a diffraction angle (2θ±0.1) of 4.7, 5.5, 7.3, 8.6, 14.5 and 16.7 degrees.

3. A pharmaceutical composition which comprises, as an active ingredient, a crystal according to claim 1.

4. A pharmaceutical composition which comprises, as an active ingredient, a crystal according to claim 2.

5. A method for treating a disease associated with hyperglycemia, which comprises administering to an individual in need of said treatment a therapeutically effective amount of a crystal according to claim 1.

6. A method for treating a disease associated with hyperglycemia, which comprises administering to an individual in need of said treatment a therapeutically effective amount of a crystal according to claim 2.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: PCR primer 0702F

<400> SEQUENCE: 1
atggaggagc acacagaggc                                                    20

<210> SEQ ID NO 2
<211> LENGTH: 20
<212> TYPE: DNA
<213> ORGANISM: Artificial Sequence
<220> FEATURE:
<223> OTHER INFORMATION: PCR primer 0712R

<400> SEQUENCE: 2
ggcatagaag ccccagagga                                                    20

<210> SEQ ID NO 3
<211> LENGTH: 29
<212> TYPE: DNA
<213> ORGANISM: Artificial Sequence
<220> FEATURE:
<223> OTHER INFORMATION: PCR primer 0714F

<400> SEQUENCE: 3
aacctcgaga tggaggagca cacagaggc                                          29

<210> SEQ ID NO 4
<211> LENGTH: 29
<212> TYPE: DNA
<213> ORGANISM: Artificial Sequence
<220> FEATURE:
<223> OTHER INFORMATION: PCR primer 0715R

<400> SEQUENCE: 4
aacaagcttg gcatagaagc cccagagga                                          29
```

-continued

```
<210> SEQ ID NO 5
<211> LENGTH: 25
<212> TYPE: PRT
<213> ORGANISM: Artificial Sequence
<220> FEATURE:
<223> OTHER INFORMATION: carboxy terminal peptide of vector KL29

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25
```